United States Patent [19]

Semeraro et al.

[11] Patent Number: 4,806,533
[45] Date of Patent: Feb. 21, 1989

[54] 1,4-DIHYDRO PYRIDINE 3,5 DICARBOXYLIC ACID DERIVATIVES AND COMPOSITIONS

[75] Inventors: Claudio Semeraro, Bresso; Dino Micheli, Carpi; Daniele Pieraccioli; Giovanni Gaviraghi, both of Verona, all of Italy; Alan D. Borthwick, London, England

[73] Assignee: Glaxo, s.p.a., Verona, Italy

[21] Appl. No.: 16,590

[22] Filed: Feb. 19, 1987

[30] Foreign Application Priority Data

Feb. 20, 1986 [IT]  Italy .................. 19486 A/86

[51] Int. Cl.$^4$ ................ A61K 31/455; A61K 31/535; C07D 401/06; C07D 413/06
[52] U.S. Cl. .................. 514/211; 514/212; 514/235.5; 514/318; 514/340; 514/343; 514/356; 540/544; 540/547; 544/131; 546/144; 546/275; 546/281; 546/321
[58] Field of Search ............... 540/544, 597; 544/131; 546/194, 275, 281, 321; 514/211, 212, 236, 318, 340, 343, 356, 235.5

[56] References Cited

U.S. PATENT DOCUMENTS

3,455,945  6/1969  Loev .................... 546/321
4,492,703  1/1985  Goldmann et al. ........... 546/321

FOREIGN PATENT DOCUMENTS

1409865  10/1975  United Kingdom .

OTHER PUBLICATIONS

U.K. Patent Application GB 2,164,336 A (19 Mar. 1986), pp. 1 and 2.

*Primary Examiner*—Robert W. Ramsuer
*Attorney, Agent, or Firm*—Morgan & Finnegan

[57] ABSTRACT

Compounds are described of the formula

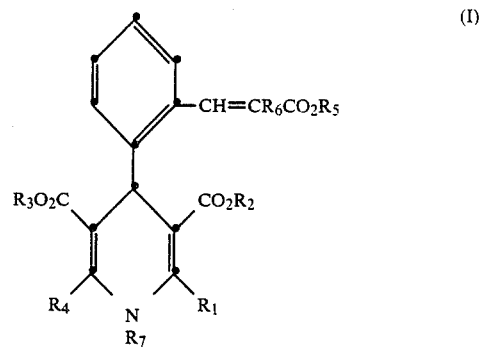

(I)

wherein
$R_1$ and $R_4$ independently represent a $C_{1-4}$ alkyl group;
$R_2$ and $R_3$ independently represent a $C_{1-6}$ straight or branched alkyl chain or alkoxy group;
$R_5$ represents a straight or branched chain $C_{1-13}$ alkyl group or a $C_{5-8}$ cycloalkyl group which may be substituted by a $C_{1-3}$ alkyl substituent;
$R_6$ represents a halogen atom or a straight or branched $C_{1-3}$ alkyl group.
$R_7$ represents a $C_{1-4}$ alkyl group [optionally substituted by hydroxy, $C_{1-3}$ alkoxy or trifluoromethyl or by a group $NR_8R_9$ where $NR_8R_9$ forms a saturated 5 to 7 membered ring optionally containing an additional heleroatom which is oxygen]; or $R_7$ represents a phenyl$C_{1-2}$alkyl group in which the phenyl portion is optionally substituted by 1 to 3 $C_{1-3}$ alkyl or $C_{1-3}$ alkoxy groups or halogen atoms.

The compounds represented by formula (I) reduce intracellular calcium ion concentration by limiting transmembranal calcium ion influx and thus may be useful for the treatment of cardiovascular disorders such as hypertension.

19 Claims, No Drawings

1,4-DIHYDRO PYRIDINE 3,5 DICARBOXYLIC ACID DERIVATIVES AND COMPOSITIONS

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. It has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders, and for the treatment of diseases characterised by reversible airway obstruction such as asthma and chronic bronchitis.

The invention thus provides for compounds of the general formula (I)

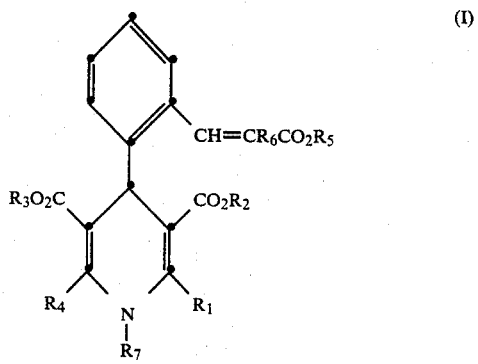

wherein
$R_1$ and $R_4$ independently represent a $C_{1-4}$ alkyl group;
$R_2$ and $R_3$ independently represent a $C_{1-6}$ straight or branched chain alkyl or alkoxyalkyl group;
$R_5$ represents a $C_{1-13}$ straight or branched chain alkyl group of a $C_{5-8}$ cycloalkyl group which may be substituted by a $C_{1-3}$ alkyl group;
$R_6$ represents a hydrogen or halogen atom or a straight or branched $C_{1-3}$ alkyl group; and
$R_7$ represents a $C_{1-4}$ alkyl group [optionally substituted by hydroxy, $C_{1-3}$ alkoxy or trifluoromethyl or by a group —$NR_8R_9$ where $NR_8R_9$ forms a saturated 5 to 7 membered ring optionally containing one additional heteroatom which is oxygen]; or $R_7$ represents an phenyl $C_{1-2}$ alkyl group in which the phenyl portion is optionally substituted by 1 to 3 $C_{1-3}$ alkyl or $C_{1-3}$ alkoxy groups or halogen atoms.

The compounds represented by formula (I) can exist in more than on isomeric and/or enantiomeric form and the invention includes all such isomers, enantiomers and mixtures thereof.

Examples of suitable groups for $R_1$ and $R_4$ independently include methyl and ethyl.

Examples of suitable groups for $R_2$ and $R_3$ independently include $C_{1-4}$ alkyl such as methyl, ethyl, isopropyl, isobutyl or tertiary butyl or $C_{1-4}$ alkyl (such as ethyl) substituted by $C_{1-3}$ alkoxy (e.g. methoxy or propoxy).

When the group $R_5$ represents a $C_{1-13}$ alkyl group this may for example be a methyl, ethyl, propyl, isopropyl, butyl, isobutyl, tertiary butyl, pentyl, isopentyl, neopentyl, hexyl, 2,6-dimethyl-4-heptyl or octyl group. When $R_6$ represents a cycloalkyl group, conveniently this represents a cyclopentyl, cyclohexyl or a cycloheptyl group which may be substituted by a methyl group.

When the group $R_6$ represent a $C_{1-3}$ alkyl group this may for example be a methyl, ethyl or n-propyl group, and is preferably a methyl or ethyl group.

When the group $R_6$ represents a halogen atom this may be for example a chlorine, bromine or iodine atom and is preferably a bromine atom.

Examples of suitable groups for $R_7$ include methyl, 2,2,2-trifluoroethyl, hydroxyethyl, phenethyl, N-pyrrolidinoethyl and N-morpholinoethyl.

The group —$CH=CR_6CO_2R_5$ in the compounds of formula (I) can exist in the (Z) or the (E) configuration and preferred compounds are those in which the hydrogen atom and the group $R_6$ are trans with respect to each other.

Preferably $R_1$ and $R_4$ represent methyl groups.
$R_2$ and $R_3$ preferably independently represent $C_{1-4}$ alkyl e.g. methyl or ethyl, more preferably ethyl.
$R_5$ preferably represents a $C_{2-9}$ alkyl group, or more preferably tert butyl.
$R_6$ preferably represents a methyl or ethyl group or more preferably a hydrogen atom.
$R_7$ preferably represents methyl or N-morpholinoethyl.

Particularly preferred compounds according to the invention are
4-[2-(3-(1,1-Dimethylethoxy)-3-oxo-1-propenyl)-phenyl]-1,4-dihydro-2,6-dimethyl-1-methyl-3,5-pyridinedicarboxylic acid diethylester
4-[2-(3-(1,1-Dimethylethoxy)-3-oxo-1-propenyl)-phenyl]-1,4-dihydro-2,6-dimethyl-1-[2-(1-morpholino)ethyl]-3,5-pyridinedicarboxylic acid diethylester
and more particularly the E isomers thereof.

The ability of compounds of the invention to limit or inhibit the effect of calcium ions on the tone of vascular smooth muscle may be determined using a depolarised rabbit ear artery prepared according to the method of Towart. R. et al Br. J. Pharmacol. 1982, 75, 1508.

The antihypertensive activity of compounds of the invention was demonstrated by intravenous and/or oral administration of the compound to male spontaneously hypertensive rats.

The compounds of the invention are thus of interest in the treatment of hypertension and diseases characterised by reversible airways obstruction such as asthma and chronic bronchitis.

They are also potentially useful for the treatment of other cardiovascular disorders including angina pectoris, myocardial ischaemia, congestive heart failure, cerebral vascular and peripheral disorders.

The compounds of the invention may be formulated in a conventional manner for use with one or more pharmaceutical carriers or excipients.

Thus a further aspect of the invention includes pharmaceutical compositions the compounds of formula (I) and/or physiologically acceptable addition salts thereof formulated for oral, sub lingual, transdermal, parenteral or rectal administration, or for administration by inhalation or insufflation.

For oral administration the pharmaceutical composition may take the form of for example tablets, which may be film or sugar coated, capsules, powders, granules, solutions including syrups, or suspensions prepared by conventional means with acceptable excipients. For sub lingual administration the composition may take the form of tablets or lozenges formulated in the conventional manner.

A proposed daily dosage of active compound of the invention for the treatment of man is in the range of 0.03 mg to 100 mg, which may conventionally be administered in one or more doses. The precise dose employed will depend on the age of condition of the patient as well as the rout of administration.

For oral use the compounds of the invention are conveniently administered to the human patient at a dose in the range 0.3 to 100 mg per day. For parenteral use the compounds of the invention are conveniently administered at a dose in the range of 0.03-30 mg per day.

For administration by inhalation use the compounds of the invention are conveniently administered to the human patient at a dose in the range of 0.1 mg to 10 mg per day.

For oral use the compound is preferably administered twice or more particularly once a day.

Methods for preparing the compounds of formula (I) are described below and for the intermediates described below $R_1$–$R_7$ have the meanings defined above for compounds of formula (I) or are such groupings in a protected form unless otherwise stated.

Thus according to one general process (1) the compounds of formula (I) may be prepared by reaction the $\alpha,\beta$-unsaturated ketone (II) with the aminoester (III). The reaction is conveniently carried out in a solvent such as an alkanol, e.g. ethanol or isopropanol and preferably with heating e.g. 40°–150° C.

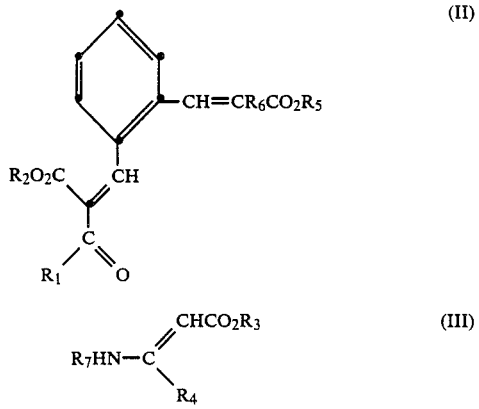

The $\alpha,\beta$-unsaturated ketone (II) may be prepared by reacting the aldehyde (IV) with the ketoester (V), in a solvent such as an alkanol e.g. ethanol or isopropanol, preferably with heating e.g. 40°–150° C. Conveniently this reaction is carried out in the presence of a catalyst such as piperidine acetate.

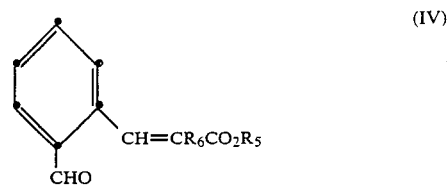

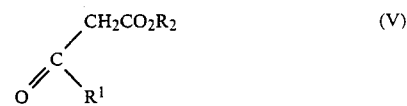

In a modification of this process for preparing compounds of formula (I), the aldehyde (IV) may be reacted with a mixture of the aminoester (III) and the ketoester (V) under the conditions previously described for the reaction of the $\alpha,\beta$-unsaturated ketone (II) with the aminoester (III).

Compounds of formula (I) and in particular the E isomers thereof in which $R_1$ and $R_4$ are the same and $R_2$ and $R_3$ are the same may be prepared by reacting the aldehyde (IV) with the aminoester (III) in the presence of a suitable acid catalyst. Examples of suitable acid catalysts include organic acids such as oxalic acid, alkanoic acids e.g. acetic acid or haloalkanoic acids such as trichloroacetic acid or trifluoroacetic acid or pyridinium salts thereof, or a sulphonic acid such as an alkanesulphonic acid e.g. methanesulphonic acid or an arylsulphonic acid e.g. benzenesulphonic acid or p-toluenesulphonic acid or a tetrahaloboric acid such as tetrafluoroboric acid. The reaction is preferably carried out in the presence of a solvent and at a temperature within the range of −70° to 30° C. preferably −30° to 10° C. Suitable solvents for the reaction include aprotic solvents such as hydrocarbons, e.g. hexane or cyclohexane, acetonitrile or ethers such as tertiary butyl methyl ether, dioxan or tetrahydrofuran, or protic solvents such as an alkanol e.g. methanol, ethanol, propanol, isopropanol or butanol.

Compounds of formula (I) and more particularly the E isomers thereof in which $R_1$ and $R_4$ are the same and $R_2$ and $R_3$ are the same may also be prepared by reacting the aldehyde (IV) with the ketoester (V) and an amine $R_7NH_2$ (VI) or a salt thereof, e.g. the hydrochloride. This reaction is conveniently carried out in a solvent such as pyridine with heating at 50°–120° C., conveniently at reflux.

Compounds of formula (IV) may be prepared by reacting the bis aldehyde (VII) with the triphenylphosphorane (VIII) in solvent such as methylene chloride or toluene.

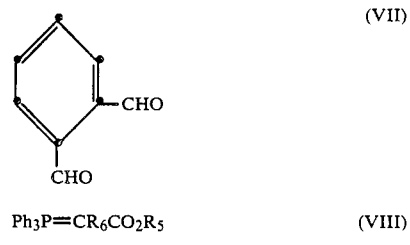

Compounds of formula (IV) may also be prepared by reacting a 2-halobenzaldehyde (IX)

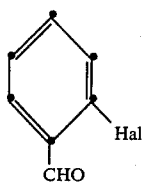
(IX)

(where Hal represents a bromine or iodine atom) with an acrylic ester $CH_2=CR_6CO_2R_5$ (X), in the presence of a catalytic amount of a palladium salt such as palladium acetate, in the presence of a suitable organic base such as a trialkylamine e.g. triethylamine or tri-n-butylamine. The reaction is also preferably carried out in the presence of a triarylphosphine such as tri-o-tolyphosphine, or more preferably, triphenylphosphine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

The compounds of formulae (III), (V), (VI), (VII), (VIII), (IX) and (X) are either known compounds or may be made by analogous processes to those used for known compounds.

According to another general process (2) the compounds of formula (I) may be prepared from compounds of formula (I) in which $R_7$ represents hydrogen by standard alkylation procedures using an alkylhalide $R_7Hal$ (XI) (where Hal represents a halogen atom e.g. iodine).

The reaction is carried out in a solvent such as an amide e.g. dimethylformamide in the presence of an alkali metal hydride (e.g. sodium hydride) or an alkali metal alkoxide.

The compounds of formula (I) in which $R_7$ represents hydrogen may be prepared according to the method of general process (I) using a compound of formula (III) in which $R_7$ is a hydrogen atom.

The compounds of formula (XI) are either known compounds or may be made by analogous methods to those used for known compounds.

According to another general process (3) compounds of formula (I) in which the hydrogen atom and the group $R_6$ in the moiety $-CH=CR_6CO_2R_5$ are trans with respect to each other may prepared from compounds of formula (XII)

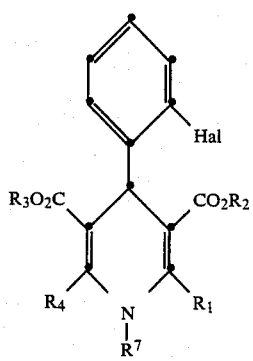
(XII)

(where Hal represents bromine or iodine) by reaction with an acrylic ester

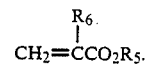

The reaction takes place in the presence of a catalytic amount of palladium salt such as palladium acetate in the presence of a suitable organic base such as trialkylamine e.g. triethylamine or tri-n-butylamine. The reaction is also preferably carried out in the presence of a triarylphosphine such as tri-o-tolyphosphine or triphenylphosphine.

The reaction is conveniently carried out in the suitable solvent such as xylene or t-butyl acetate, or more conveniently in dimethylformamide or in a mixture of solvents e.g. xylene/dimethylformamide, preferably with heating. The reaction mixture is preferably heated within the range of 60° to 150° C., more preferably at 80° to 110° C.

Compounds of formula (XII) in which $R_7$ is as defined in formula (I) may be prepared by alkylating the corresponding compounds of formula (XII) in which $R_7$ represent a hydrogen atom according to the method of general process (2).

The compound of formula (XII) in which $R_7$ represents a hydrogen atom or a group as defined in formula (I) may be prepared by reacting the 2-halobenzaldehyde (IX) with the aminoester (III) (where $R_7$ is a hydrogen atom or a group as defined in formula (I)) and/or the ketoester (V) according to the conditions described above for the reaction between the compounds of formula (IV) and the aminoester (III) and/or the ketoester (V).

The following examples illustrate the invention. Temperatures are in °C.

INTERMEDIATE 1

4-(2-Bromophenyl)-1,4-dihydro-2,6-dimethyl-3,5-pyridinecarboxylic acid, diethyl ester

INTERMEDIATE 2

(E)-4-(2-(3-(1,1-Dimethylethoxy)-3-oxo-1-propenyl)-phenyl 1,4-dihydro-2,6-dimethyl-3,5-pyridinedicarboxylic acid, diethyl ester

INTERMEDIATE 3

4-(2-Bromophenyl)-1,4-dihydro-2,6-dimethyl-1-[2-(1-morpholinyl)]ethyl-3,5-pyridinedicarboxylic acid diethyl ester A suspension of sodium hydride (80% in mineral oil) (0.65 g) in DMF (5 ml) was cooled to 0° and a solution of Intermediate (1) (3 g) in DMF was added dropwise over 30 min, keeping the temperature at 15° or less. After the addition was complete, N-(2-chloroethyl) morpholine hydrochloride (2.7 g) was added in portions over 25 min, keeping the temperature at approximately 15°. The mixture was heated at 80° for 3 h and after cooling to room temperature the reaction mixture was poured in water and extracted with ethyl acetate. The organic phase was dried over anhydrous $Na_2SO_4$ and filtered. Evaporation of the solvent and crystallisation from ethyl acetate gave the title compound (1.2 g) as a white solid. M.p. 130°–135°. T.l.c. (ethyl acetate/diethyl ether 1:1) Rf 0.4.

EXAMPLE 1

4-(E)-[2-(3-(1,1-Dimethylethoxy)-3-oxo-1-propenyl)-phenyl]-1,4-dihydro-2,6-dimethyl-1-methyl-3,5-pyridinedicarboxylic acid diethylester A suspension of sodium hydride (80% in mineral oil) (0.15 g) in dimethylformamide (3 ml) was cooled to 0° and a solution of Intermediate (2) (1.5 g) in DMF was added dropwise over 30 mins, keeping the temperature at 15° or less. After the addition was complete, methyl iodide (0.31 ml) in DMF was added dropwise, keeping the temperature at approximately 15°. The mixture was stirred at room temperature for 15 min and then poured into water and extracted with ethyl acetate. The organic phase was dried over $Na_2SO_4$ and filtered. Evaporation of the solvent and crystallization from ethyl acetate yielded the title compound (0.7 g) as white crystals. M.p. 149°–151°. T.l.c. (petrol/ethyl acetate 6:4) Rf 0.5

EXAMPLE 2

4-(E)-[2-(3-(1,1-Dimethylethoxy)-3-oxo-1-propenyl)-phenyl]-1,4-dihydro-2,6-dimethyl-1-[2-(1-morpholino)ethyl]-3,5-pyridinedicarboxylic acid diethylester A mixture of Intermediate 3 (i) (1 g), tertiary butylacrylate (0.4 ml), palladium acetate (4 mg), triphenylphosphine (20 mg), tri-butylamine (0.57 ml) and DMF (2 ml) was heated in a capped bottle at 100° C. for 24 h. The cooled solid reaction mixture was poured in ethyl acetate, filtered off and the clear solution obtained was evaporated to dryness to leave a brown oil. Flash chromatography of the oil eluting with ethyl acetate/petroleum ether 8:2 gave the title compound (640 mg) as white solid. M.p. 175°–177°. T.l.c. (ethyl acetate) Rf 0.3

We claim:

1. Compound of the general formula (I)

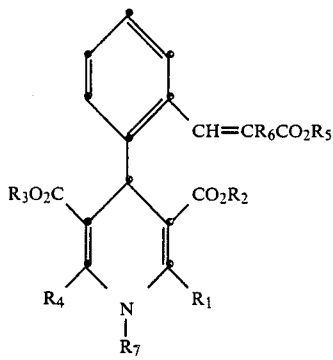

in which $R_1$ and $R_4$ independently represent a $C_{1-4}$ alkyl group;
$R_2$ and $R_3$ independently represent a $C_{1-6}$ straight or branched chain alkyl or alkoxyalkyl group;
$R_5$ represents a $C_{1-13}$ straight or branched chain alkyl group or a $C_{5-8}$ cycloalkyl group which may be substituted by a $C_{1-3}$ alkyl group;
$R_6$ represents a hydrogen or halogen atom or a straight or branched $C_{1-3}$ alkyl group; and
$R_7$ represents a $C_{1-4}$ alkyl group substituted by a group $—NR_8R_9$ where $NR_8R_9$ forms a saturated 5 to 7 membered ring optionally containing one additional heteroatom which is oxygen.

2. Compounds as claimed in claim 1 in which $R_1$ and $R_4$ independently represent methyl or ethyl groups.

3. Compounds as claimed in claim 1 in which $R_2$ and $R_3$ independently represent a methyl or ethyl group.

4. Compounds as claimed in claim 3 in which $R_2$ and $R_3$ each represent an ethyl group.

5. Compounds as claimed in claim 1 in which $R_5$ represents a $C_{2-9}$ alkyl group.

6. Compounds as claimed in claim 5 in which $R_5$ represents a tert butyl group.

7. Compounds as claimed in claim 1 in which $R_6$ represents a hydrogen atom.

8. Compounds as claimed in claim 1 in which $R_7$ represents N-pyrrolidinoethyl or N-morpholinoethyl group.

9. Compounds as claimed in claim 8 in which $R_7$ represents a N-morpholinoethyl group.

10. The compound 4-[2-(3-(1,1-dimethylethoxy)-3-oxo-1-propenyl)phenyl]-1,4-dihydro-2,6-dimethyl-1-[2-(1-morpholino)ethyl]-3,5-pyridinedicarboxylic acid diethylester.

11. Compounds as claimed in claim 1 in which the hydrogen atom and the group $R_6$ in the moiety $—CH=CR_6CO_2R_5$ are trans with respect to each other.

12. Compounds as claimed in claim 1 in which $R_1$ and $R_4$ independently represent methyl or ethyl groups, $R_2$ and $R_3$ independently represent a methyl or ethyl group, $R_5$ represents a $C_2$–$C_9$ alkyl group, $R_6$ represents a hydrogen atom, and $R_7$ represents N-pyrrolidinoethyl or N-morpholinoethyl.

13. Compounds as claimed in claim 12 in which $R_2$ and $R_3$ each represent an ethyl group.

14. Compounds as claimed in claim 12 in which $R_5$ represents a tert butyl group.

15. Compounds as claimed in claim 12 in which $R_7$ represents N-morpholinoethyl group.

16. Compounds as claimed in claim 12 in which the hydrogen atom and the group $R_6$ in the moiety $—CH=CR_6CO_2R_5$ are trans with respect to each other.

17. Compounds as claimed in claim 12 in which $R_1$ and $R_4$ each represent a methyl group, $R_2$ and $R_3$ each represent an ethyl group, $R_5$ represents a tert butyl group, and $R_7$ represents N-morpholinoethyl group, and in which the hydrogen atom and the group $R_6$ in the moiety $—CH=CR_6CO_2R_5$ are trans with respect to each other.

18. Pharmaceutical compositions comprising a compound as claimed in claim 1 in association with a pharmaceutically acceptable carrier or diluent.

19. Compositions as claimed in claim 18 in a form suitable for oral, sub lingual, transdermal, parenteral or rectal administration, or for administration by inhalation or insufflation.

* * * * *